US008088969B2

(12) United States Patent
Elliott et al.

(10) Patent No.: US 8,088,969 B2
(45) Date of Patent: Jan. 3, 2012

(54) SWINE POPULATION HAVING LOW LEVELS OF PORCINE ENDOGENOUS RETROVIRUS AND USES THEREOF

(75) Inventors: Robert Bartlett Elliott, Auckland (NZ); Olga Garkavenko, Auckland (NZ); Alexander Burns Ferguson, Auckland (NZ)

(73) Assignee: Living Cell Products Pty Ltd., Sydney (AU)

( * ) Notice: Subject to any disclaimer, the term of this patent is extended or adjusted under 35 U.S.C. 154(b) by 942 days.

(21) Appl. No.: 11/911,653

(22) PCT Filed: Apr. 13, 2006

(86) PCT No.: PCT/NZ2006/000074
§ 371 (c)(1),
(2), (4) Date: Dec. 19, 2007

(87) PCT Pub. No.: WO2006/110054
PCT Pub. Date: Oct. 19, 2006

(65) Prior Publication Data
US 2008/0152625 A1   Jun. 26, 2008

(30) Foreign Application Priority Data
Apr. 15, 2005 (NZ) ........................................ 539491

(51) Int. Cl.
*C12N 5/00* (2006.01)
(52) U.S. Cl. ............................. 800/8; 435/325; 424/93.7
(58) Field of Classification Search ........................ None
See application file for complete search history.

(56) References Cited

U.S. PATENT DOCUMENTS

| | | | |
|---|---|---|---|
| 6,355,859 B1 * | 3/2002 | Bosworth et al. | ................. 800/8 |
| 6,469,229 B1 | 10/2002 | Sachs et al. | |
| 6,610,288 B1 | 8/2003 | Edge et al. | |
| 6,867,347 B2 | 3/2005 | Patience | |

FOREIGN PATENT DOCUMENTS

| | | |
|---|---|---|
| NZ | 532057 | 6/2006 |
| WO | WO 00/66188 | 11/2000 |
| WO | WO 01/52871 | 7/2001 |
| WO | WO 02/32437 | 4/2002 |
| WO | WO 03/002746 | 1/2003 |
| WO | WO 03/027270 | 4/2003 |
| WO | WO 2004/113516 | 12/2004 |

OTHER PUBLICATIONS

Tucker A et al. 2002. The production of transgenic pigs for potential use in clinical xenotransplantation: microbiological evaluation. Xenotransplantation 9: 191-202.*
Robins JH et al. 2003. The origins of the feral pigs on the Auckland Islands. J Royal Soc NZ 33: 561-69.*
Allan et al. (2000) "Porcine Circoviruses: A Review," *J. Vet. Diag. Invest.* 12:3-14.
Armstrong, A. (Jul. 11, 2004) "Pig Parts: Xenotransplantation," *Radio National Program Transcript* 16 pages, http://www.abc.net.au/rn/talks/bbing/stories/s1153112.htm.
Brewer et al. (2001) "Porcine Encephalomyocarditis Virus Persists in Pig Myocardium and Ifects Human Myocardial Cells," *J. Virol.* 75(23):11621-11629.
Blusch, J.H. (202) "Pig Endogenous Retrovirus and Xenotransplantation," *Xenotransplantation* 9(4):242-251.
Dorling, A. (2002) "Clinical Xenotransplantation: Pigs Might Fly," *Am. J. Transplant.* 2(8():695-700.
Ehlers et al. (1999) "Detection of Two Novel Porcine Herpesviruses with High Similarity to Gammaherpesviruses," *J. Gen. Virol.* 80:971-978.
Erker et al. (1999) "Rapid Detection of Hepatitis E Virus RNA by Reserve Transcription-Polymerase Chain Reaction Using Universal Oligonucleotide Primers," *J. Virol. Methods* 81:109-113.
Garkavenko et al. (2001) "Detection and Characterization of Swine Hepatitis E Virus in New Zealand," *J. Med. Virol.* 65(3):525-529.
Garkavenko et al. (2004) "Monitoring for Potentially Xenozoonotic Viruses in New Zealand Pigs," *J. Med. Virol.* 72:338-344.
Gemeniano et al. (2006) "The Infectivity and Host Range of the Ectopic Porcine Endogenous Retrovirus, PERV-C, id Modulated by Residues in the C-Terminal Region of its Surface Envelope Protein," *Virology* 346(1):108-117.
Hamel et al. (1999) "PCR Assay for Detecting Porcine Cytomegalovirus," *J. Clin. Microbiol.* 37:3767-3768.
Hattermann et al. (2004) "Infection Studies on Human Cell Lines with Porcine Circovirus Type 1 and Porcine Circovirus Type 2," *Xenotransplantation* 11:284-294.
Ho et al. (1995) "Infections in Transplant Recipients," In; *Mandell, Douglas and Bennett's Principles and Practice of Infectious Diseases*, Mandell et al. eds., New Yourk: Churchill Livingstone, pp. 35-107.
International Search Report, Corresponding to International Application No. PCT/NZ2006/000074, Mailed Jun. 27, 2006.
Kiupel et al. (2001) "Viral Replication and Lesions Isolated from a Pig with Post weaning Multisystemic Wasting Disease," *Vet. Pathol.* 38:74-82.
Larochelle et al. (1999) "Typing of Porcine Circovirus in Clinical Specimens by Multiplex PCR," *J. Virol. Methods* 80:69-75. Le Tissier et al. (1997) "Two Sets of Human-Tropic Pig Retrovirus," *Nature* 389:681-682.
Mills et al. (1999) "Long-Term Studies on Hantavirus Reservoir Populations in the Southwestern United States: A Synthesis," *Emerg. Infect. Dis.* 5:135-142.
Mueller et al. (2002) "Activation of Cytomegalovirus in Pig-to-Primate Organ Transplantation," *J. Virol.* 76:4734-4740.
Niemann, H. (2001) "Current Status and Perspectives for the Generation of Transgenic Pigs for Xenotransplantation," *Ann. Transplant.* 6(3):6-9.
O'Connor et al. (2001) "Multiple Porcine Circovirus 2-Associated Abortions and Reproductive Failure in a Miltisire Swine Production Unit," *Can. Vet. J.* 42:551-553.
Patience et al. (1997) "Infection of Human Cells by an Endogenous Retrovirus of Pigs," *Nat. Med.* 3:282-286.

(Continued)

Primary Examiner — Lora E Barnhart Driscoll
(74) Attorney, Agent, or Firm — Greenlee Sullivan P.C.

(57) ABSTRACT

The invention relates to methods of selecting and maintaining a population of pigs having a low copy number of porcine endogenous retrovirus, and the use of such pigs as a source of cells, tissue and/or organs suitable for xenotransplantation. The invention further relates to methods for selecting cells, tissue and/or organs from such pigs for suitability for use in xenotransplantation.

12 Claims, 1 Drawing Sheet

OTHER PUBLICATIONS

Patience et al. (2002) "Porcine Endogenous Retrovirus—Advances, Issues and Solutions," *Xenotransplantation* 9(6):373-375.

Rodrigez-Arrioja et al. (1999) "Aujesky's Disease Virus Infection Concurrent with Postweaning Multisystemic Wasting Syndrome in Pigs," *Vet. Rec.* 144:152-153.

Takeuchi et al. (1998) "Host Range and Interferences Studies of Three Classes of Pigs Endogenous Retrovirus," *J. Virol.* 72:9986-9991.

Tischer et al. (1995) "Presence of Antibodies Reacting with Porcine Circovirus in Sera of Humans, Mice, and Cattle," *Arch. Virol.* 140:1427-1439.

Tiscu.er et al. (1974) "Characterization of Papovavirus- and Picornavirus-Like Particles in Permanent Pig Kidney Cell Lines," *Zentralblatt fur Bacteriologie Microbiologie and Hygiene seres A* 26:153-167.

Ulrich et al. (1999) "Characterization of the DNA Polymerase Loci of the Novel Porcine Lymphotropic Herpesviruses 1 and 2 in Domestic and Feral Pigs," *J. Gen. Virol.* 80(12):3199-3205.

Vanderhallen er al. (1998) "Identification of Enchephalomyocarditis Virus in Clinical Samples by Reverse Transcription-PCR Followed by Genetic Typing Using Sequence Analysis," *J. Clin. Microbiol.* 36:3463-3467.

* cited by examiner

SWINE POPULATION HAVING LOW LEVELS OF PORCINE ENDOGENOUS RETROVIRUS AND USES THEREOF

CROSS-REFERENCE TO RELATED APPLICATIONS

This application is the U.S. National Stage of International Application No. PCT/NZ2006/000074, filed Apr. 13, 2006 and published in English on Oct. 19, 2006 as WO 2006/110054 A1, which claims the benefit of New Zealand Application 539491, filed Apr. 15, 2005; all of which are hereby incorporated by reference in their entirety to the extent not inconsistent with the disclosure herein.

FIELD OF THE INVENTION

The present invention relates to methods of selecting and maintaining a population of pigs having a low copy number of porcine endogenous retrovirus, and the use of such pigs as a source of cells, tissue and/or organs suitable for xenotransplantation. The invention further relates to methods for selecting cells, tissue and/or organs from such pigs for suitability for use in xenotransplantation.

BACKGROUND OF THE INVENTION

Organ transplantation is an effective therapy for end-stage organ failure, but is severely limited by a shortage of donor organs. Numerous people die each year while waiting for an organ. In addition to the difficulty in obtaining donor organs, the expense of organ transplantation also limits the number of organ transplant operations carried out.

The possibility that animals could provide an alternative source of donor organs and tissues has stimulated much debate. Xenotransplantation clearly has the potential to alleviate the suffering and mortality associated with donor organ shortages, yet certain safety concerns are associated with the procedure. Concerns include infectious risk to the recipient of the xenotransplant, and to those in contact with the recipient and thence the wider public.

The most serious concern is the possibility of transmission of infectious agents including microorganisms from the xenotransplant to the recipient, and the consequent potential for the emergence of a new human infection and possibly disease. A major reason that pigs are considered the donor animal of choice in preference to non-human primates is due to the reduced microbiological burden that they carry. It should be noted that the risk of transmission of microorganisms is not unique to xenotransplantation. Many cases have been documented of transmission of organisms causing disease during allotransplantation procedures.

Cross-species infection (zoonosis) is, however, of particular concern when compared to transmission within a species because the behaviour of an infectious organism in the xenotic host cannot be predicted by its pathogenicity in its natural host. Organisms considered to be benign in their natural host can cause significant morbidity in a zoonotic scenario. Examples include the potentially fatal infections of humans with the Nipah virus of pigs, herpes B virus of primates and hantavirus of rodents (1).

The risk of cross-species infection is also enhanced because the xenotransplant recipient is generally immunosuppressed.

The microorganisms that could be transferred along with the organ, tissue or cell population vary in their potential to establish an infection in the recipient. Viruses such as pig lymphotropic herpesvirus (PLHV), pig cytomegalovirus (PCMV), and pig circovirus (PCV), all of which are highly prevalent in pig populations (see, for example, 2) are able to establish persistent infections and are considered to be potentially oncogenic. Data on activation of cytomegalovirus in pig-to-primate organ transplantation suggests that PCMV may be an important pathogen in immunosuppressed xenograft recipients (3). It has also been reported that PCV type 2 can be transmitted to human cells in vitro (4).

However, the greatest risk of infection may come from those organisms that have an ability to be transferred as an asymptomatic latent entity within the organ. Such organisms include endogenous retroviruses (ERV), and herpesviruses. Pig endogenous retroviruses (PERVs) have been a major source of anxiety and represent possibly the most important safety concern for xenotransplantation as it has been reported that two of the three families of PERV infect human cells in vitro (5).

Unlike other infectious organisms that a pig may carry, PERV viruses are not transmitted between animals as an infectious agent but rather are inherited by all animals as part of their germ-line DNA. Thus, these viruses form part of the genome and are therefore present in every cell. The amount of virus present varies between pig species, but it has been asserted that on average approximately 50 copies of the virus are present in every cell and conventional breeding techniques are not able to remove these viruses from pig populations (6). The presence of infectious organisms, and particularly PERV viruses, in pig cells is thus a potential barrier to the future of xenotransplantation.

It would therefore be desirable to have a method for producing pig cells, tissue and/or organs suitable for xenotransplantation that are significantly reduced in organisms that may be able to be transmitted to a human recipient and thereby significantly reduce the risk of xenozoonotic infection. More specifically, it would be desirable to produce pig cells, tissues and/or organs for xenotransplantation which have a low PERV copy number, thereby minimising the risk of transmission to the xenotransplant recipient. It is an object of the invention to go some way towards achieving these desiderata and/or to provide the public with useful choice.

SUMMARY OF THE INVENTION

It has surprisingly been found that the Auckland Island herd of pigs have a unique advantage over other breeds of pig with respect to endogenous microorganisms. In particular, this herd contains a novel subgroup of animals that have unusually low copy numbers of PERV. It is therefore contemplated that selective breeding of these animals will produce progeny having a further reduced microorganism content, including PERV copy number. Such pigs would thus be particularly suitable for xenotransplantation.

Accordingly, in a first aspect the present invention provides a method of breeding a herd of pigs that are free of infectious microorganisms and have a PERV copy number between 0 and 30, said method comprising the steps:

(a) selecting male and female Auckland Island swine having a favourable microorganism profile,
(b) mating male and female swine selected in step (a),
(c) selecting progeny produced by step (b) that have a favourable microorganism profile and a PERV copy number between 0 and 30;

whereby the progeny selected in step (c) are suitable for use in xenotransplantation.

The male and/or female swine of step (b) and/or the progeny of step (c) may have a PERV copy number of preferably between 0 and 25; between 0 and 20; between 0 and 18; between 0 and 16; between 0 and 14; between 0 and 12; between 0 and 10; between 0 and 8; between 0 and 7; or between 0 and 6; and most preferably between 0 and 5.

The favourable microorganism profile of step (a) and step (c) comprises no detectable levels of hepesvirus, porcine lymphotrophic herpesvirus (PLHV), pig cytomegalovirus (PCMV), encephalomyocarditis virus (EMCV), pig circovirus (PCV), hepatitis E virus (HEV), Toxoplasma, eperythrozoon, brucella, listeria, mycobacterium TB, leptospirillum, haemophilus suis, any virus causing porcine respiratory reproductive syndrome, any virus causing rabies, any virus causing pseudorabies, parvovirus, encephalomyocarditus virus, any virus causing swine vesicular disease, porcine polio virus (techen), any virus causing hemagglutinating encephalomyocarditus, swine influenza type A, adenovirus, transmissible gastroenteritis virus and vesicular stomatitis virus.

Male and female progeny selected in step (c) may be mated in step (b) to produce further progeny for use in xenotransplantation in order to maintain the herd.

The method may optionally include additional screening for particular blood groups to match either a potential xenotransplant recipient or to match the antigen profile of serum used in in vitro culture to reduce tissue rejection and/or cell damage by immune reactions.

Preferably, the swine selected in step (a) and more preferably the progeny selected in step (c) are of blood group O.

Preferably, the swine selected in step (a) and more preferably the progeny selected in step (c) are lacking PERV-C.

More preferably, the swine selected in step (a) and more preferably still the progeny selected in step (c) are of blood group O and lacking PERV-C.

The method may optionally include additional screening for immunogenic antigens present in cell surfaces, such as MHC Class I antigen, again to reduce organ, tissue or cell rejection or damage in vivo or in vitro.

The invention further provides one or more pigs produced by a method of the invention.

In a second aspect, the present invention provides one or more pigs free of infectious microorganisms and having a PERV copy number between 0 and 30, wherein said one or more pigs are produced by a method comprising the steps:
(a) selecting male and female Auckland Island swine having a favourable microorganism profile,
(b) mating male and female swine selected in step (a),
(c) selecting progeny produced by step (b) that have a favourable microorganism profile and a PERV copy number between 0 and 30.

In a third aspect, the present invention provides one or more pigs free of infectious microorganisms and having a PERV copy number between 0 and 30 and of blood group O and/or lacking PERV-C, wherein said one or more pigs are produced by a method comprising the steps:
(a) selecting male and female Auckland Island swine having a favourable microorganism profile,
(b) mating male and female swine selected in step (a),
(c) selecting progeny produced by step (b) that have a favourable microorganism profile and a PERV copy number between 0 and 30.

In another aspect, the present invention provides organs, tissues or cells isolated from one or more pigs produced by the method of the invention, said organs, tissues or cells being free of infectious microorganisms and having a PERV copy number between 0 and 30, and are particularly suitable for transplantation into a xenogeneic subject, including a human subject.

Preferably, the one or more organs, tissues and cells are isolated from one or more pigs, wherein said one or more pigs are neonatal pigs of from 7 to 21 days old.

The organs, tissues and cells may be selected or isolated from the group consisting of liver, lung, heart, brain, pancreas, muscle, blood, bone, testes and ovary.

Preferably, the organs for whole organ xenotransplantation are selected from liver, lung and heart.

Preferably, the tissues and cells for xenotransplantation are selected from pancreatic islets, hepatocytes, non-parenchymal liver cells, gall bladder epithelial cells, gall bladder endothelial cells, bile duct epithelial cells, bile duct endothelial cells, hepatic vessel epithelial cells, hepatic vessel endothelial cells, sinusoid cells, choroid plexus cells, fibroblasts, Sertoli cells, adrenal chromaffin cells, and muscle cells.

The present invention also provides an implantable composition comprising at least one isolated pig organ, tissue or cell of the present invention together with a pharmaceutically acceptable carrier.

The composition may further comprise feeder cells such as fibroblasts or Sertoli cells isolated from the pigs produced by the method of the invention.

The invention further provides the use of at least one isolated organ, tissue or cell isolated from one or more pigs produced by the method of the invention, said organ, tissue or cell being free of infectious microorganisms, and having a PERV copy number between 0 and 30, in the preparation of an implantable composition or device for treating a patient suffering from or predisposed to a disease, disorder or condition associated with a deficiency in or absence of organ function.

Preferably the at least one isolated organ, tissue or cell is isolated from a neonatal pig of from 7 to 21 days old.

According to a further aspect of the invention, there is provided a method of treating a patient suffering from or predisposed to a disease, disorder or condition associated with a deficiency in or absence of organ tissue or cell function, comprising the implantation in a patient in need thereof of an organ, tissue or cell isolated from one or more pigs produced by a method of the invention According to a further aspect of the invention there is provided a method of treating a patient suffering from or predisposed to a disease, disorder or condition associated with a deficiency in or absence of organ function comprising administering an effective amount of one or more implantable compositions of the invention, to a patient in need thereof.

In one embodiment, said deficiency or absence is in or of liver function and the implantable composition comprises hepatocytes, non-parenchymal liver cells, gall bladder cells, bile duct cells, hepatic vessel cells or sinusoid cells. In an alternative embodiment, said deficiency or absence is in or of pancreatic function and the implantable composition comprises pancreatic islet cells. In an alternative embodiment, said deficiency or absence is in or of neurological function and the implantable composition comprises choroid plexus cells.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

DETAILED DESCRIPTION OF THE INVENTION

Figure 1:
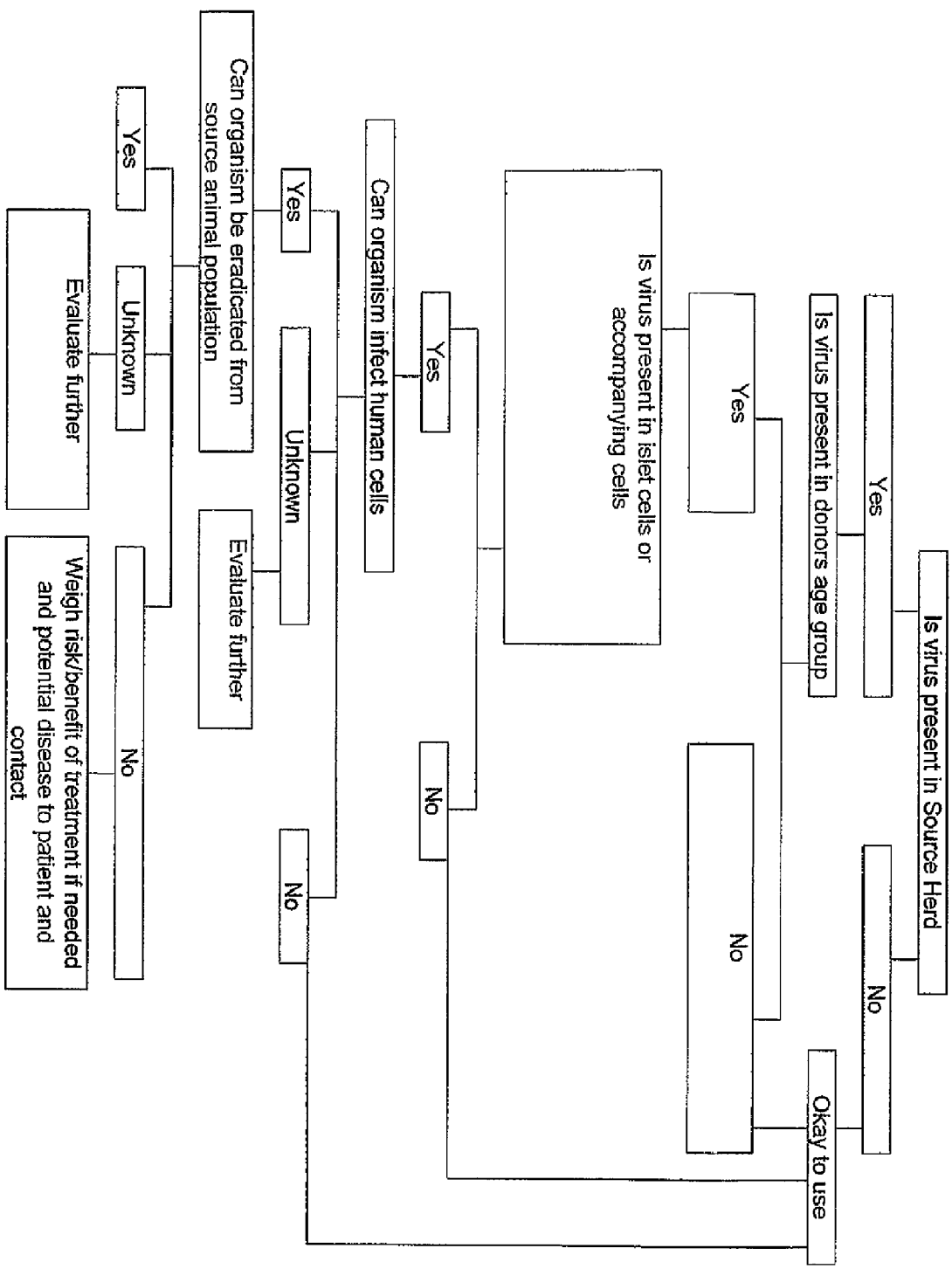
FIG. 1 depicts diagrammatically a method for virus identification within a pig population and thus a means for the selection of suitable female and male pigs for breeding and maintaining a herd of pigs according to the present invention.

The present invention is directed to the selection of a pig donor herd which are free of infectious microorganisms and, in particular, have a PERV copy number between 0 and 30 (and preferably between 0 and 5). Such pigs would be an especially suitable source of organs, tissues and cells for xenotransplantation.

There have been previous attempts to provide swine suitable for xenotransplantation. For example, U.S. Pat. No. 6,867,347 (6) discloses a herd of inbred swine reportedly defective for transmission of porcine endogenous retrovirus (PERV). However, the average PERV copy number amongst this herd is high, with reportedly approximately 50 copies of the virus in every cell. Additionally, the infectious microorganism status of this herd is not disclosed, and is it known whether these swine are free of each of the common porcine viruses PCMV, PLHV, EMCV, HEV, and PCV type 1 and type 2.

Similarly, U.S. Pat. No. 6,469,229 (7) discloses inbred miniature swine that are homozygous for a major histocompatibility complex haplotype. Again, however, the average PERV copy number amongst this herd is high, and the infectious microorganism status of this herd is not disclosed, nor is it established that these swine are free of all of the common porcine viruses described above.

Surprisingly, the applicants have now determined that a New Zealand inbred strain of pig have a surprisingly low number of copies of the ubiquitous retrovirus, porcine endogenous retrovirus (PERV). This strain of pig are also free of the common pig infectious viruses including PCMV, PLHV, EMCV, HEV and PCV.

This strain has been resident on the remote Auckland Islands, a sub-Antarctic island group south of New Zealand, being effectively isolated for about 200 years, and are referred to herein as AI pigs.

Endogenous retroviruses (ERVs) have been reported as being a constituent of the normal DNA of every vertebrate species tested including pigs and humans. The normal retrovirus lifecycle includes the stable integration of retroviral genetic material into the host cell chromosomal DNA. Where the host cell is a germ-line cell, the viral nucleic acid material (or provirus) will subsequently be inherited by all offspring in a manner typical of any other Mendelian gene. It has been proposed that if the presence of a particular provirus in the DNA of a germ-line cell places the offspring at a selective disadvantage it would not be expected to survive over evolutionary time periods and this ERV is not expected in the ongoing gene pool. The ERV present in the germ-line of animals today tend not to be pathogenic for their own species. Individual ERV loci also tend to be replication defective due to mutations present in their genome. However, it has further been proposed that the potential exists for individual defective loci to interact by complementation and recombination to form infectious virus. While ERVs may not be pathogenic for their normal host species, the very same viruses can change their pathogenicity when interspecies transmission occurs.

It has been asserted that all porcine cells, including those isolated from the NIH minipig, Yucatan, multiple land breeds, and the animals currently being used in clinical trials, with the single exception of the cell line ST-IOWA, appear to produce PERV capable of infecting and replicating in human cells (6). More recently, cells from various pig breeds have been assessed for the presence of infectious PERV particles and several have been identified which do not appear to contain infectious PERV particles, see for example, those shown in Table I below.

TABLE I

Presence of infectious PERV in various pig breeds

| Pig Breed | Cells | Infectious PERV |
|---|---|---|
| Landrace | endothelial cells | + |
| Landrace | islets | + |
| Large White/Landrace | islets | + |
| Miniature swine | PBMC | + |
| Large White | Islets | − |
| Yorkshire | PBMC | − |
| | fetal neuronal cells | − |
| Miniature swine D/D | PBMC | − |
| Cambrough | PBMC, Sertoli, islets | − |

PBMC = peripheral blood mononuclear cells

It has further been asserted that while the use of a specific-pathogen-free (SPF) breeding program would eliminate most pathogens that might be transmitted during xenotransplantation, pathogens such as PERV that are transmitted through the germ-line would not be eliminated, so that one of the potential risks from the use of pig organs is the transmission of such pathogens (6).

Of principal importance, the applicants have now determined that the AI pigs described herein exhibit unusually low copy numbers of porcine endogenous retrovirus (PERV), lower than any previous reports. Furthermore, experiments described herein show no evidence of the production of infectious PERV particles, nor has PERV transmission in vitro using co-cultures or transmission in vivo to xenotransplant recipients been observed, when using cells from AI pigs selected by the methods of the present invention.

Accordingly, in a first aspect the present invention provides a method of breeding a herd of pigs that are free of infectious microorganisms and have a PERV copy number between 0 and 30, said method comprising the steps:

(a) selecting male and female Auckland Island swine having a favourable microorganism profile,
(b) mating male and female swine selected in step (a),
(c) selecting progeny produced by step (b) that have a favourable microorganism profile and a PERV copy number between 0 and 30;

whereby the progeny selected in step (c) are suitable for use in xenotransplantation.

Three different classes of PERV exist: PERV-A, PERV-B, and PERV-C. These classes refer to differences in the envelope region of PERV. The viral envelope is the major determinant of host range and is essential for infection. The two main types of pig retrovirus, PERV-A and PERV-B, are widely distributed in different pig breeds (8). PERV-A and PERV-B viruses have wider host ranges, including several human cell lines, than PERV-C viruses, which infected only two pig cell lines (9). Recently it has been shown that PERV-A and PERV-C can recombine and form a variant with new infectious characteristics (10).

It would be desirable for a donor pig to be lacking PERV-C so as to prevent any possible recombination with existent PERV-A. Preferably, the selection process would include breeding pigs that lack the PERV-C variant, and/or selecting donor progeny that lack the PERV-C variant.

The swine are free of infectious microorganisms, and are maintained as such by methods well-known in the animal husbandry art to minimize ingress of potential pathogens.

Such methods include barrier husbandry and isolation, in addition to specialized breeding techniques such as hysterotomy derivation in suitable containment units. Preferably, the maintenance of the infectious microorganism-free status of the herd includes regular monitoring of the herd for infectious microorganisms. Methods to determine the presence or absence of infectious microorganisms are well known in the art, and include immunological assays, and nucleic acid detection assays, such as PCR-based detection methods.

Methods to determine the presence or absence of infectious microorganisms can be used to determine the microorganism profile of an animal so as to assess, for example, its suitability for inclusion in the breeding method of the invention, or its use as a xenotransplant donor. The favourable microorganism profile of step (a) and step (c) comprises no detectable levels of hepesvirus, PLHV, PCMV, EMCV, PCV, HEV, Toxoplasma, eperythrozoon, brucella, listeria, mycobacterium TB, leptospirillum, haemophilus suis, any virus causing porcine respiratory reproductive syndrome, any virus causing rabies, any virus causing pseudorabies, parvovirus, encephalomyocarditus virus, any virus causing swine vesicular disease, porcine polio virus (techen), any virus causing hemagglutinating encephalomyocarditus, swine influenza type A, adenovirus, transmissible gastroenteritis virus, and vesicular stomatitis virus.

An exemplary method for determining the suitability of a potential donor herd for xenotransplantation is shown in FIG. 1. This exemplary method includes a determination of whether a pathogen is present in the source country, and if so, in the source herd. If it is present in the source herd, it should be determined if the pathogen is present in the donor group, and specifically, in the organs, tissues or cells to be transplanted. It is also important to establish whether the pathogen can be transmitted to a recipient cell, for example a human cell, and so to a recipient, for example, a human.

Use of the selected animals, and in particular the progeny of such breeding, as a donor source herd for xenotransplantation is preferred as the low PERV copy number, coupled with a lack of transmissible PERV, is safer than the use of donors having higher PERV copy numbers.

The applicants believe, without wishing to be bound by any theory, that by using the breeding method of the invention, for example in an iterative manner, it will be possible to breed and select from each successive generation progeny having further decreased PERV copy number. The applicants further believe, again without wishing to be bound by any theory, that in such a way it will be possible to breed and select progeny having no copies of PERV in their genome.

The AI pigs described herein are also free of a number of porcine viruses reportedly endemic or ubiquitous amongst pig populations worldwide.

For example, pig cytomegalovirus (PCMV) is a betaherpesvirus (Herpesviridae family), and it is regarded as a ubiquitous virus with at least 98% of all tested pigs in the United Kingdom reportedly infected (11). PCMV has been isolated from the respiratory tract of pigs and may be associated with atrophic rhinitis or inclusion body rhinitis, a common disease syndrome affecting recently weaned pigs. Post-weaning sneezing and evidence of mild rhinitis is purportedly very common in New Zealand pigs. The importance of human CMV infection in allogeneic transplant recipients has raised concerns that pig cytomegalovirus might behave similarly in xenotransplant recipients (12).

Importantly, the applicants have determined that the AI herd described herein is free of PCMV. Therefore, transmission of PCMV from organs, tissues or cells obtained from an AI herd donor to a xenotransplant recipient cannot occur.

In another example, pig lymphotropic herpesvirus (PLHV) infection has been reported to be endemic, with virus present in commercial herds (13). PLHV belongs to subfamily of gammaherpesviruses (Herpesviridae). The basic properties of these herpesviruses, including infectivity for other species, are not yet determined. Phylogenetically they are purportedly close to ovine and bovine lymphotropic herpesviruses which cause lymphoproliferative disease in their hosts (14).

Importantly, the applicants have determined that the AI herd described herein is negative for PLHV. Therefore, transmission of PLHV from organs, tissues or cells obtained from an AI herd donor to a xenotransplant recipient cannot occur.

Encephalomyocarditis virus (EMCV) (Picornaviridae) is a widely distributed virus belonging to the *Cardiovirus* genus. Interspecies infections with EMCV are recognised to occur, and pig EMCV can infect human myocardial cells (15). It has been reported that EMCV is present in New Zealand (16).

The applicants have determined that the AI herd described herein is negative for EMCV. Therefore, transmission of EMCV from organs, tissues or cells obtained from an AI herd donor to a xenotransplant recipient cannot occur.

Hepatitis E virus (HEV) was recently removed from the family Caliciviridae and is currently unclassified. There is growing evidence that pig HEV may be zoonotic. Therefore, this virus must be excluded before tissue is used for xenotransplantation.

The applicants have determined that the AI herd described herein is free of HEV. Therefore, transmission of HEV from organs, tissues or cells obtained from an AI herd donor to a xenotransplant recipient cannot occur.

Pig circovirus (PCV) belongs to the Circiviridae family. Porcine circovirus was first discovered in 1974 as a contaminant of the continuous porcine kidney cell line, PK15 (17), and subsequent serological studies in pig sera from Germany, Canada, New Zealand, Great Britain, Northern Ireland and the USA have reported 25% to 98% positivity for PCV1 antibodies in fattening and adult pigs (18). It has been suggested that PCV infection is ubiquitous throughout the world. No associated disease has been identified. There are, however, several contradictory reports on the zoonotic properties of pig circovirus. Antibodies reacting with PCV type 1 have been reported in human, mice and cattle (18). About 20% of healthy adults and 30% of hospitalised patients in Germany, and 24% of hospitalised patients in Canada were reported seropositive to PCV-like antigen. However, neither virus nor viral genome has been detected in any mammalian species other than pigs. It has been proposed that the PCV1 antibody reactivity found in humans and other species may be non-specific.

A new strain of porcine circovirus, named porcine circovirus type 2, has been found in pigs with postweaning multisystemic wasting syndrome (PMWS) (19). PMWS most frequently affects 5-12-week-old piglets and is characterised by progressive weight loss, jaundice and respiratory signs. PCV2 has recently been associated with myocarditis in stillborn piglets (20). It is clear that additional studies are required to clarify the pathogenesis of PCV2-associated diseases in pigs. It has been reported that PCV2 can infect human cells in vitro (21), and BALB/c mice in the experimental setting (22). This finding has a particular importance for xenotransplantation and associated infection risk.

The applicants have determined that the AI herd described herein is free of PCV1 and PCV2. Therefore, transmission of PCV1 or PCV2 from organs, tissues or cells obtained from an AI herd donor to a xenotransplant recipient cannot occur.

The applicants have also determined that the AI herd described herein is free from the infectious vesicular diseases that affect pigs (foot and mouth disease, vesicular stomatitis, vesicular exanthema and swine vesicular disease), rabies, *Brucella suis*, swine fever, pseudorabies and spongiform encephalopathies, in addition to about 45 different pathogens many of which are common problems in veterinary practice. It is therefore apparent that the AI herd described herein has characteristics capable of rendering individual animals selected therefrom particularly suitable for use as a donor source herd for xenotransplantation.

Methods to determine or observe PERV copy number include various genomic screening methods and other methods known in the art to be suitable to determine or observe the number of copies of a particular nucleic acid sequence in the genome of an organism. Examples of such methods are presented herein in the examples.

The present invention further provides organs, tissues or cells isolated from one or more pigs produced by the method of the invention, said organs, tissues or cells being free of infectious microorganisms and having a PERV copy number between 0 and 30, and are particularly suitable for transplantation into a xenogeneic subject, including a human subject.

The said one or more pigs are free of infectious microorganisms including pathogens which affect humans, and include, but are not limited to, one or more of pathogens from the following categories of pathogens: parasites, bacteria, mycoplasma, and viruses. The swine can be free from, for example, parasites such as toxoplasma and eperytherozoon, or mycoplasma, such as M. hyopneumonia. Examples of bacteria from which the swine can be free include brucella, listeria, mycobacterium TB, leptospirillum, and haemophilus suis. Additionally, the swine can be free from viruses such as zoonotic viruses, viruses that can cross the placenta in pregnant sows, and neurotropic viruses. Zoonotic viruses include, for example, a virus in the rabies virus group, a herpes-like virus which causes pseudorabies, encephalomyocarditus virus, swine influenza Type A, transmissible gastroenteritus virus, parainfluenza virus 3 and vesicular stomatitis virus. Viruses that can cross the placenta include, for example, viruses that cause porcine respiratory reproductive syndrome, a virus in the rabies virus group, a herpes-like virus which causes pseudorabies, parvovirus, a virus that causes swine vesicular disease, techen (porcine polio virus), hemmaglutinating encephalomyocarditus, cytomegalovirus, suipoxvirus, and swine influenza type A. Neurotropic viruses include, for example, a virus in the rabies virus group, a herpes-like virus which causes pseudorabies, parvovirus, encephalomyocarditus virus, a virus which causes swine vesicular disease, porcine poliovirus (techen), a virus which causes hemmaglutinating encephalomyocarditus, adenovirus, parainfluenza 3 virus. Specific examples of viruses from which the swine are free include: a virus which causes (or results in) porcine respiratory reproductive syndrome, a virus in the rabies virus group, a herpes-like virus which causes pseudorabies, parvovirus, encephalomyocarditus virus, a virus which causes swine vesicular disease, porcine poliovirus (techen), a virus which causes hemmaglutinating encephalomyocarditus, cytomegalovirus, swine influenza type A, adenovirus, transmissible gastroenteritus virus, a virus which causes bovine viral diarrhea, and vesicular stomatitis virus.

In one embodiment, the said one or more pigs are free of the following organisms: hepesvirus, Toxoplasma, eperythrozoon, brucella, listeria, mycobacterium TB, leptospirillum, haemophilus suis, any virus causing porcine respiratory reproductive syndrome, any virus causing rabies, any virus causing pseudorabies, parvovirus, encephalomyocarditus virus, any virus causing swine vesicular disease, porcine polio virus (techen), any virus causing hemagglutinating encephalomyocarditus, suipoxvirus, swine influenza type A, adenovirus, transmissible gastroenteritus virus, and vesicular stomatitis virus.

The organs, tissues or cells isolated from said one or more pigs may be obtained from embryonic (i.e., fetal), newborn (neonatal), and adult pigs. In most cases, where a porcine organ is to be the subject of xenotransplantation, an adult organ will be utilized particularly as its greater size makes it more amenable to isolation, handling and implantation.

Neonatal tissues or cells will be generally be preferred for xenotransplantation as their isolation is typically less problematic than their fetal counterparts, whilst their survival following isolation, for example, in tissue culture or following xenotransplantation, is commonly better than adult tissues or cells. For pigs, the neonatal period is generally held to be the first 7 to 21 days following birth. Neonatal organs similarly will be generally be preferred for xenotransplantation to their fetal counterparts as their isolation is typically less problematic.

Typically, embryonic porcine organs, tissues or cells are isolated during selected stages of gestational development. For example, organs, tissues or cells can be isolated from an embryonic pig at a stage of embryonic development when the cells, tissue or organ can be recognized, or when the degree of growth and/or differentiation of the cells, tissues or organs is suitable for the desired application. For example, the organs, tissues or cells are isolated between about day twenty to about day twenty-five of gestation and birth of the pig.

The isolated cells of the invention can be maintained as a functionally viable cell culture. Examples of the methods by which cells of the invention can be cultured are presented in WO 01/52871 (23); WO 02/32437 (24); WO 2004/113516 (25); WO 03/027270 (26); WO 00/66188 (27) and/or NZ 532057/532059/535131 (28), incorporated herein in their entirety. Media which can be used to support the growth of porcine cells include mammalian cell culture media, for example, Dulbecco's minimal essential medium, and minimal essential medium. The medium can be serum-free but is preferably supplemented with animal serum such as fetal calf serum, or more preferably, porcine serum (ie autologous serum).

When isolated from a donor swine, the cells of the invention retain their phenotype and/or are capable of performing their function. For example, porcine liver cells of the invention are capable of, among other functions, proliferating, secreting plasma proteins, such as albumin, and factor VIII, and expressing low density lipoprotein receptors and thus, binding low density lipoproteins. Preferably, isolated cells are capable of maintaining differentiated functions in vitro and in vivo, and adhering to substrates, such as culture dishes.

Preferably, the said one or more pigs are of a blood group that does not induce or minimizes complement mediated immediate humoral rejection on transplantation into the recipient. Pigs have only two blood groups, A and O. The presence of blood group A antigen, coupled with the absence of antibodies to this antigen, is indicative of blood group A. The absence of blood group A antigen, coupled with the presence of antibodies to this antigen, is indicative of blood group O. The Applicants have determined that the AI herd shows polymorphism for blood group A and for carbohydrate-containing surface antigens. Preferably, organs, tissues or cells used for xenotransplation are obtained from blood group O donors.

The blood group O phenotype is inherited as a Mendelian recessive trait in which the mating of:
AA×AA swine results in 100% blood group A litter;
AA×AO swine results in 100% blood group A litter (probability of 50% being AO heterozygotes);
AA×OO swine results in 100% blood group A litter (AO);
AO×AO swine results in litter with 75% probability being blood group A (25% AA and 50% AO) and 25% blood group O (OO);
OO×AO swine results in litter with 50% probability being blood group A (AO) and 50% blood group O (OO);
OO×OO swine results in 100% blood group O litter.

Preferably, the selective breeding method of the invention produces progeny that have, in addition to low PERV copy number, cells that comprise surface antigens that do not induce or minimize complement mediated rejection in recipients. For example, the selective breeding methods of the invention preferably produce progeny of blood group O. To produce progeny of blood group O, it is therefore necessary that both pigs to be mated are carriers of the O allele. Preferably at least one and more preferably both of the pigs to be mated are of blood group O (homozygous for the O allele). See Example 4 herein.

Methods to determine the blood group of mammals are well known in the art, and representative methods suitable to determine the blood group of swine are presented herein in the Examples.

The organs, tissues or cells obtained from the said one or more pigs can be encapsulated or otherwise isolated from the recipient's immune system as described herein to inhibit rejection of the tissues or cells upon transplantation into a xenogeneic recipient. Immunosuppression, for example using immunosuppressive drugs well known in the art such as those described in U.S. Pat. No. 6,610,288 (29) (incorporated herein in its entirety) will typically be utilized in the case of transplanted porcine organ(s). Prior to introduction into a subject, the tissues or cells can be modified to inhibit immunological rejection, for example as described in (29).

Accordingly, the invention provides an implantable composition comprising at least one isolated pig organ, tissue or cell of the present invention together with a pharmaceutically acceptable carrier.

The compositions of the invention can be inserted into a delivery device which facilitates introduction of the cells and/or compositions into the subject. Such delivery devices include tubes, e.g., catheters, for infusing or injecting cells and fluids into the body of a recipient subject. In one embodiment, the tubes additionally have a needle, e.g., a syringe, through which the cells of the invention can be introduced into the subject at a desired location. The compositions of the invention can be inserted into such a delivery device, e.g., a syringe, e.g., syringe pump, in different forms. For example, the cells can be suspended in a solution or embedded in a support matrix when contained in such a delivery device. As used herein, the term "solution" includes a pharmaceutically acceptable carrier or diluent in which the cells of the invention remain viable. Pharmaceutically acceptable carriers and diluents include sterile saline and aqueous buffer solutions. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating porcine cells as described herein in a pharmaceutically acceptable carrier or diluent and, as required, other ingredients recited above, followed by filtered sterilization.

Compositions and devices of the invention comprising organs, tissues or cells of the invention suitable for implantation facilitate the survival of the cells upon implantation. In the case of xenotransplanted cells, this will commonly be achieved by protecting the cells from exposure to the recipient's immune system. In particular, the invention deals with the use of compositions and devices in:

Alginate-encapsulated form—to provide additional immune protection of the transplanted procine cells. The methodology for microencapsulating porcine neonatal islet cells and transplanting same is set out in (23)—such alginate encapsulation provides efficient, safe, and functional methods for xenotransplantion.

Subcutaneous implant devices that allow the development of a prevascularised allogeneic collagen reservoir for the placement of the porcine cell compositions. Preferably, the implant device is cell-impermeable but protein or secreted factor-permeable, such as the "TheraCyte" device available from TheraCyte, Inc., Irvine, Calif.

Matrix preparations—in which porcine cell compositions are cultured on gelatin, collagen and/or other matrices supplemented with natural carbohydrate polymers.

Plasma Thrombin Clot—Allogeneic plasma clots produced with allogeneic thrombin as a biocompatible containment device.

Compositions and devices of the invention may utilise support matrices in which the porcine cells can be incorporated or embedded include matrices which are recipient-compatible and which degrade into products which are not harmful to the recipient. Natural and/or synthetic biodegradable matrices are examples of such matrices. Natural biodegradable matrices include collagen matrices. Synthetic biodegradable matrices include synthetic polymers such as polyanhydrides, polyorthoesters, and polylactic acid. These matrices provide support and protection for the cells in vivo.

The invention accordingly further provides a method of treating a patient suffering from or predisposed to a disease, disorder or condition associated with a deficiency in or absence of organ function comprising administering an effective amount of one or more implantable compositions of the invention, to a patient in need thereof.

The invention also provides a method of treating a patient suffering from or predisposed to a disease, disorder or condition associated with a deficiency in or absence of organ, tissue or cell function, comprising the implantation in a patient in need thereof of an organ, tissue or cell isolated from one or more pigs produced by a method of the invention Such treatment methods of the invention are preferably able to restore or augment cell, tissue or organ function in a xenotransplant recipient whilst minimising the risk of transmission of xenozoonotic infectious agents, including PERV. The number of cells or amount of tissue required for transplantation, the frequency of transplants etc required to restore or augment organ, tissue, or cell function would be known by skilled workers from prior art methods.

The organs, tissues, cells, compositions and treatment methods of the instant invention are useful for long-term, physiologically-responsive provision of organ, tissue or cell function due to the organs, tissues and all remaining viable and secreting the required biological factors.

The tissues, cells, compositions and treatment methods of the present invention are particularly suitable for xenotransplantation, being free of xenozoonotic infectious agents and having a reduced PERV copy number. Cell implantation therapy has an advantage over traditional organ transplantation therapies in that the availability of cells suitable for implantation is not limited as are suitable organs from cadaveric or live organ donors.

In addition, whilst cells which are to be implanted may be foreign to the host, various methods have been developed to prevent the host immune system from attacking and thereby causing the death of the implanted cells, such as, for example, placing cells in aggregates or devices that provide a physical barrier between the cells and the host's immune system ((23), (24), (25), (26), (27) and (28)).

Accordingly, the invention provides isolated porcine organs, tissues or cells which are suitable for administration to a xenogeneic recipient. These organs, tissues or cells can be used to treat disorders which are characterized by deficient or absent organ, tissue or cell function. As used herein, the term "isolated" refers to an organs, tissues or cells which have been separated from their natural environment. This term includes gross physical separation from the natural environment, e.g., removal from the donor animal, and alteration of the organs', tissues' or cells' relationship with the neighboring cells with which they are in direct contact by, for example, dissociation.

As used herein, the term "porcine" is used interchangeably with the terms "pig" and "swine" and refers to mammals in the family Suidae. Such mammals include wholly or partially inbred swine, preferably those members of the Auckland Island pig herd herein described.

The term "treating" as used herein includes reducing or alleviating at least one adverse effect or symptom of a disease, disorder or condition associated with a deficiency in or absence of organ, tissue or cell function. For example, in the case of diseases, disorders or conditions associated with a deficiency in or absence of pancreatic function, examples of adverse effects or symptoms include high blood glucose, obesity, aberrant glucose sensitivity and/or glucose insensitivity, aberrant insulin levels, diabetic microvascular and macrovascular disease, aberrant lipase secretion, aberrant secretin levels, aberrant cholecystokinin levels, steatorrhea, aberrant gastrin levels, and aberrant cholinergic and/or adrenergic function.

Accordingly, the tissues, cells or compositions of the invention are transplanted into a patient suffering from or predisposed to a disease, disorder or condition associated with a deficiency in or absence of organ, tissue or cell function in an amount such that there is an at least partial reduction or alleviation of at least one adverse effect or symptom of the disease, disorder or condition.

As used herein the terms "administering", "introducing", and "transplanting" are used interchangeably and refer to the placement of the organs, tissues, cells or compositions of the invention into a subject, e.g., a xenogeneic subject, by a method or route which results in localization of the organs, tissues, cells or compositions of the invention at a desired site. The organs, tissues, cells or compositions of the invention can be administered to a subject by any appropriate route which results in delivery of the cells to a desired location in the subject where at least a portion of the cells remain viable. It is preferred that at least about 5%, preferably at least about 10%, more preferably at least about 20%, yet more preferably at least about 30%, still more preferably at least about 40%, and most preferably at least about 50% or more of the cells remain viable after administration into a subject. The period of viability of the cells after administration to a subject can be as short as a few hours, e.g., twenty-four hours, to a few days, to as long as a few weeks to months. Methods of administering, introducing and transplanting organs, tissues, cells or compositions of the invention are well-known in the art. Cells can be administered in a pharmaceutically acceptable carrier or diluent.

The term "recipient" as used herein refers to mammals, particularly humans, suffering from or predisposed to a disease, disorder or condition associated with a deficiency in or absence of organ, tissue or cell function. The term "recipient" also includes mammals in which an immune response is elicited against allogeneic or xenogeneic cells. Examples of recipients include primates (e.g., humans, and monkeys). A "xenogeneic recipient" (also referred to herein as "recipient subject" or "subject") as used herein is a recipient into which cells of another species are introduced or are to be introduced.

As used herein, the language "disease, disorder or condition associated with a deficiency in or absence of organ, tissue or cell function" includes a disorder in which there is abnormal organ function. Such abnormal organ function includes an impairment or absence of a normal organ function or presence of an abnormal organ function.

The invention consists in the foregoing and also envisages constructions of which the following gives examples only and in no way limit the scope thereof.

Example I

This example details the characterization of the viral status of the low PERV copy number AI pig herd.

Materials and Methods

Nucleic Acid Extraction.

Porcine materials processed included tissue, peripheral blood mononuclear cells, plasma, and faeces.

Extraction from tissues: tissue samples (30 mg) for RNA extraction were homogenised with 1 ml of TRIZOL reagent (GIBCO/BRL, Gaitherburg, Md.) or lysis buffer from the Qiagen Rneasy Kit (Qiagen) using a glass homogeniser (Wheaton). RNA was extracted using the Qiagen Rneasy Kit (Qiagen) or TRIZOL reagent (GIBCO/BRL, Gaitherburg, Md.). DNA from tissue was extracted using Puregene DNA Isolation Kit (Gentra) in accordance with the manufacturer's recommendations.

Extraction from blood cells: DNA from peripheral blood mononuclear cells (PBMCs) was extracted with the Purogene Isolation Kit (Gentra). RNA from PBMCs was isolated with TRIZOL reagent (GIBCO/BRL, Gaitherburg, Md.).

Extraction from faeces. RNA from faeces was extracted with TRIZOL reagent (GIBCO/BRL, Gaitherburg, Md.) in accordance with the manufacturer's protocol.

Polymerase Chain Reaction (PCR).

All polymerase chain reactions (PCR) were carried out using a Perkin Elmer GeneAmp PCR System 2400 thermocycler.

PCMV PCR: We have used PCMV PCR developed by Hamel (30). Sensitivity of both PCR and nested PCR was estimated using cellular DNA extraction from a PBMC (peripheral blood mononuclear cells) of infected pigs. The sensitivity was determined by limiting dilution as being $10^{-2}$ g of DNA per reaction.

PLHV PCR: PCR developed by Ehlers (31) was used for PLHV identification. The sensitivity of PLHV PCR was estimated by limited dilution using PBMC DNA extracted from infected pigs. The sensitivity of the PLHV PCR was estimated to be $10^{-4}$ µg of DNA per reaction.

EMCV RT-PCR: PCR developed by Vanderhallen & Koenen (32) was used for the virus identification. Sensitivity of the RT-PCR was determined by limited dilution of RNA extracted from cell culture infected with EMCV. Sensitivity was estimated as being $10^{-2}$ g of RNA per reaction.

PCV PCR: PCR designed by Larochelle (33) was used for virus identification. Primers for nested PCR have been designed in our laboratory. Forward primer was 5'-TGTTACAAAGTTATCATCTAGAATAA-3', reverse primer was 5'-CAAGGCTACCACAGTCACAAC-3'. The sensitivity of PCV PCR was estimated by limited dilution using DNA extracted from tissues (lung, liver) of infected pigs. The sensitivity of the PCV PCR was estimated to be $10^{-6}$ µg of DNA per reaction.

HEV Reverse Transcription and PCR: PCR designed by Erker (34) was used for the viral identification. Sensitivity of the RT-PCR was determined by limited dilution of RNA extracted from faeces of infected pigs. Sensitivity was estimated as being $10^{-2}$ µg of RNA per reaction.

Sequence Analysis of PCR Products.

To check the specificity of a particular PCR, amplified products were purified using the High Pure PCR Product Purification Kit (Boehringer) according to the manufacturer's protocol and then sequenced on an ABI 373A sequencer (Centre for Gene Technology, Auckland University). Computer analysis was performed by BLASTN and DNASTAR programs.

ELISA for Detecting HEV Antibody.

Pig IgG HEV antibody was measured with an ELISA kit using recombinant GST-ORF2.1 as the immobilized antigen. Alternatively, IgG HEV antibody was measured with an enzyme immunoassay (EIA) as previously described (13).

Animals and Tissues.

Pigs tested were from New Zealand commercial herds (Large White and Cambrough pig breeds), a high-health-status (HHS) herd (Cambrough breed), and feral pigs resident on the remote Auckland Islands (the AI herd).

The porcine tissues analyzed included blood, liver, spleen, pancreas, lung, and heart from one-week-old piglets. Faeces, blood and peripheral blood mononuclear cells (PBMC) were analysed from older pigs. All tissues were collected during surgery and snap frozen in liquid nitrogen, and then stored at −70° C. before analysis. Blood from 1-week-old piglets was collected by heart puncture and 5 ml placed into acid-citrate dextrose (ACD) or EDTA tubes. Blood from 20-week-old piglets and sows was collected from the jugular vein into EDTA tubes. Faeces from pigs were collected in sterile containers and kept on ice. Faeces were processed on the day of collection. Two samples of boar semen were used for the PCV testing. All animal procedures were carried out in accordance with Institutional animal welfare rules.

For each virus under consideration, a range of tissues from pigs of various ages were examined.

Results

Pig Cytomegalovirus (PCMV).

PBMC from 15 twenty-week-old pigs and sows from the HHS herd and AI pigs were analyzed for PCMV. Lung, liver and spleen from 10 one-week-old piglets from the HHS herd and 5 piglets from the AI herd were also analysed. Seventy percent of PBMC samples from sows and 20-week-old piglets were positive. PBMC, lung, liver and spleen from one-week-old piglets and extracted islets cells were all negative for PCMV DNA (Table II). AI pigs all tested negative for the virus.

TABLE II

Results of PCMV testing

| Age of pig | No. of pigs | Source herd | Tissues analyzed | Results |
|---|---|---|---|---|
| 1 week | 10 | HHS | Lung, liver, spleen PBMC | Not detected |
| 1 week | 5 | AI | Lung, liver, spleen PBMC | Not detected |
| >20 weeks | 15 | HHS | PBMC | 70% positive |
| >6 months | 20 | AI | PBMC | Not detected |

Pig Lymphotrophic Herpes Virus (PLHV).

PBMC were analysed for PLHV from 5 one-week-old piglets and 10 twenty-week-old pigs of the HHS herd, also from 20 six month old AI pigs and 10 pigs more than 6 months old from a commercial herd. Lung, liver PBMC and spleen from 10 one-week-old piglets from the HHS herd and from 5 one-week-old AI piglets were also analysed. In initial tests positive controls were deliberately omitted to avoid any possibility of contamination. In the HHS herd, 95% of twenty-week-old pigs showed viral DNA in PBMC (Table III). Phylogenetic analysis of amplicons revealed 100% similarity with PLHV type 2 (2). No evidence of PLHV type I was found. One-week-old piglets were negative for the viral DNA. AI pigs were negative for PLHV virus.

TABLE III

Results of PLHV testing

| Age of pig | No. of pigs | Source herd | Tissues analyzed | Results |
|---|---|---|---|---|
| 1 week | 10 | HHS | PBMC, lung, liver, spleen | Not detected |
| 1 week | 5 | HHS | PBMC | Not detected |
| 1 week | 5 | AI | lung, liver, spleen | Not detected |
| 20 weeks | 10 | HHS | PBMC | 95% positive |
| 6 months | 20 | AI | PBMC | Not detected |
| >6 months | 10 | commercial | PBMC | 95% positive |

Encephalomyocarditis Virus (EMCV).

Piglets from the HHS and AI herds were analysed for EMCV.

HHS herd: myocardial tissue from 20 one-week-old piglets and faeces from 11 ten-to-twelve-week-old piglets were tested.

AI herd: myocardial tissue from 3 one-week-old piglets, and faeces from 10 twelve-to-fourteen-week-old pigs were tested. No evidence of EMCV was found in the myocardium of 1-week-old piglets or in faeces of post-weaned pigs (Table IV).

TABLE IV

Results of ECMV testing.

| Age of pig | No. of pigs | Source herd | Tissues analyzed | Results |
|---|---|---|---|---|
| 1 week | 20 | HHS | Heart | Not detected |
| 10 to 14 weeks | 11 | HHS | Faeces | Not detected |
| 12-14 weeks | 10 | AI | Faeces | Not detected |
| 1 week | 3 | AI | Heart | Not detected |

Pig Circovirus Type 1 and 2 (PCV).

The following tissues were examined:

HHS herd: 14 faecal samples from 14 to 16-week-old pigs, 4 lung tissues, and 4 faecal samples from one-week-old pigs.

Commercial herd: 14 faecal samples from 14 to 6-week-old pigs.

AI herd: 10 faeces samples from adult pigs.

PCV2 DNA was amplified from the faecal samples of the 14 to 16-week-old pigs (Table V). Faecal samples from 14-16-week-old pigs were positive in 100% cases in the commercial herd, and the HHS herd. Three out of four lung tissue samples from one-week-old pigs and four out of four faeces samples from the same pigs were positive for PCV type 2. Phylogenetic analysis of the sequenced products showed 98% homology with an already described PCV2 strain (U49186). AI pigs were free from the virus.

TABLE V

Results of PCV 2 testing

| Age of pig | No. of pigs | Source herd | Tissues analyzed | Results |
|---|---|---|---|---|
| 14-16 week | 14 | HHS | faeces | Positive |
| 14-16 week | 14 | commercial | faeces | Positive |
| 1 week | 4 | HHS | faeces, lung | Positive |
| >6 months | 10 | AI | faeces | Not detected |

Hepatitis E Virus (HEV).

HEV antibody was tested in serum from 24 sows, 23 one-week-old and 25 twenty-week-old pigs from the HHS herd, 66 sera from 22 pigs from commercial herds, and six 6-month-old AI pigs. Faecal samples from 21 ten-week-old, 7 twelve-week-old, and 17 seven-week-old piglets from a commercial herd and the HHS herd were tested for HEV RNA.

HEV was present in the HHS herd and was preferentially isolated from 12-week-old piglets. Sequencing of the virus revealed that the New Zealand swine strain segregates with human HEV strains from non-endemic areas. AI pigs were free from the virus.

Example 2

This example presents the determination of PERV copy number of exemplary members of the Auckland Island herd.

Methods

Two techniques were used to calculate PERV proviral number in the pig genome: LightCycler (Roche), and PCR limiting dilution assay (PLDA) with computational analysis using QUALITY (Rodrigo et al, ubik.microbiol.washington.edu/computing).

Results

Both techniques gave good concordance with respect to proviral insert numbers. The average copy number in the AI herd was 14 or 19 by LightCycler and PLDA, respectively.

It was also established that PERV copy number varies between individual pigs within the AI herd. PERV copy number varied from 3 to 37 (37, 16, 10, 4, 12, 16, 20, 3, 14) copies by LightCycler, and from 4 to 30 copies by PLDA. It was shown that all three classes of PERV (PERV-A, -B, -C) were present in members of the AI herd.

PERV is present in the genome of every breed of swine. Most commonly, approximately 50 copies of the virus are present in every cell (6). The above data was compared with the PERV copy number in an inbred HHS pig herd and a commercial pig herd. Average copy number in the HHS herd was 43 (30, 56) and 30 in a commercial herd.

Thus, selection of male and female pigs with the lowest PERV copy number for breeding will provide a donor pig herd of exceptionally low PERV copy number and this, together with their infectious microorganism free progeny, makes them extremely suitable for use in xenotransplantation.

Example 3

This example presents an analysis of the blood group of exemplary members of the Auckland Island herd.

Methods

Two techniques were used to determine the blood group of the swine. The first method utilized monoclonal antibodies to detect blood group antigens present in buccal tissue samples taken from exemplary members. Mouse anti-A and anti-B monoclonal antibodies from Diagnostic Scotland ALBAclone were used as primary antibodies. These primary antibodies were detected with the fluorescently-labelled antimouse IgFITC as secondary antibody.

The second method detected the presence in serum samples of antibodies that were reactive against synthetic blood group antigens present on fetal pig cells. Fetal pig cells with surface blood group A synthetic molecules (Ap) or synthetic B molecules (Bp) or nothing (Op) were tested against the serum from 65 AI pigs in an agglutination assay. Those pig serums that did not react with group Ap cell were deemed to be group A, those that reacted against Ap cells were deemed to be group O.

Results

In Situ Hybridization.

Table VI below presents the results obtained in the in situ hybridizations using anti-A and anti-B monoclonal antibodies. Fluorescent staining indicated the presence of the primary antibody, and thus, the presence of the relevant antigen in the sample.

TABLE VI

In situ hybridisation for blood group antigens in buccal tissue samples

| Slide | 1° antibody | No of images | Fluorescent Scores | ABO group |
|---|---|---|---|---|
| P | -A | 4 | 0, 2+, 3+, 1-2+ | A |
| P | -B | 2 | 0, 0 | |
| 172 | -A | 3 | 1-2+, 1-2+, 1-2+ | A |
| 172 | -B | 4 | 0, 0, 0, 0, | |
| 184 | -A | 3 | 0, 0, 0, | O |
| 184 | -B | 2 | 0, 0 | |

Agglutination Assay.

Table VIII below presents the results obtained in the agglutination assay. Agglutination indicated the presence in the serum sample of antibodies cross-reactive to the relevant blood group antigen present on the cell surface. Six degrees of agglutination were ascribed, as follows: 4=one strong agglutinate; 3=medium-strong agglutinate; 2=medium agglutinate; 1=weak agglutinate; w=very weak agglutinate; and 0=no agglutinates. The presence of an agglutinate against Ap cells was indicative of blood group O.

TABLE VIII

Agglutination results for antibodies to blood group antigens

| Sample | Ap | 22C Bp | Op | Results |
|---|---|---|---|---|
| 4 | 0 | 0 | 0 | A |
| 5 | 0 | 0 | 0 | A |
| 8 | 0 | 0 | 0 | A |
| 9 | 0 | 0 | 0 | A |
| 10 | 0 | 0 | 0 | A |
| 11 | 0 | 0 | 0 | A |
| 13 | 0 | 0 | 0 | A |
| 16 | 0 | 0 | 0 | A |
| 17 | 0 | 0 | 0 | A |
| 18 | 0 | 0 | 0 | A |
| 19 | 0 | 0 | 0 | A |
| 22 | 0 | 0 | 0 | A |
| 23 | 0 | 0 | 0 | A |
| 33 | 0 | 0 | 0 | A |
| 34 | 0 | 0 | 0 | A |
| 35 | 0 | 0 | 0 | A |
| 36 | 0 | 0 | 0 | A |
| 44 | 0 | 0 | 0 | A |
| 51 | 0 | 0 | 0 | A |
| 62 | 0 | 0 | 0 | A |
| 7 | 1 | 0 | 0 | O |
| 12 | 2 | 0 | 0 | O |
| 15 | 3 | 0 | 0 | O |
| 24 | 4 | 0 | 0 | O |
| 28 | 2 | 0 | 0 | O |
| 37 | 3 | 0 | 0 | O |
| 40 | 2 | 0 | 0 | O |
| 63 | 3 | 0 | 0 | O |
| 64 | 2 | 0 | 0 | O |
| 65 | 4 | 0 | 0 | O |

Results

This example shows that about 60% of the AI pigs tested were positive for carbohydrate-containing surface antigens indicative of blood group A. Selection of AI pigs from blood group O will be advantageous as they will be more compatible with potential xenotransplant recipients and reduce the risk of transplant rejection. In addition, selection of AI pigs that have blood group O will result in less cell damage caused by immune reaction when cells and tissues from such selected pigs are grown in culture containing serum for similarly selected (O group) pigs.

Example 4

This example presents an analysis of the blood group of progeny from a trial mating of selected members of the Auckland Island herd.

Methods

One male and one female member of the AI herd were selected for mating, on the basis of their blood group. A boar of blood group A (AO) was mated with a sow of blood group O (OO). The blood group of the progeny was then determined.

Results

This mating produced four progeny: piglet #232 (OO), piglet #233 (AO), piglet #234 (OO), and piglet #235 (OO). In this mating, the result with 75% of litter being blood group O is better than the expected odds of 50%.

Example 5

This example presents the in vitro characterization of transmission of PERV from cells isolated from donor pigs amongst the Auckland Island herd.

Methods

PERV transmission characteristics of the AI herd were investigated using in vitro co-cultures. Pig neonatal islet cells and peripheral blood mononuclear cells (PBMC) were isolated, stimulated with PHA/PMA and co-cultured with human target cell line HEK 293. Cell proliferation and RT activity were analyzed for evidence of stimulation. Blood plasma was also assessed for the presence of PERV RNA. PCR analysis was used for the evidence of PERV transmission into the target cells.

Results

After 18-20 weeks of co-culture, there was no evidence of PERV or pig cellular marker (cytochrome oxidase subunit II) in the target cell line.

Example 6

This example presents the in vivo characterization of transmission of PERV from cells isolated from donor pigs amongst the Auckland Island herd.

Methods

Neonatal porcine islet cells isolated from low PERV copy number donor pigs were encapsulated in alginate, then transplanted into cynomolgous monkeys. PERV transmission was then assessed.

Results

There was no evidence of PERV transmission into experimental animals 6 months post-transplantation.

Example 7

This example presents an analysis of the PERV copy number in progeny from a trial mating of selected members of the Auckland Island herd.

Methods

A boar and a sow from the AI herd, each with low copy numbers of PERV, were selected for mating. PERV copy numbers in the breeders and progeny were determined as described herein in Example 2. The boar and sow PERV copy numbers were determined by PLDA. The piglet copy numbers were determined by Light Cycler as described in Example 2. Both methods of determining copy numbers are comparable.

Results

The mating produced five progeny, with PERV copy numbers as shown below in Table IX.

TABLE IX

PERV copy numbers in breeders and progeny

| Breeders | | Boar | × | Sow | | |
|---|---|---|---|---|---|---|
| average PERV Copy Number/cell | | 15.3 | | 9.7 | | |
| Progeny Piglet identity | P1 | P2 | P3 | | P4 | P5 |
| average PERV Copy Number/cell | 4 | 11 | 12 | | 16 | 37 |

Hence, the mating of a low PERV copy number boar with a low PERV copy number sow results in progeny with low PERV copy numbers.

Example 8

This example presents the determination of PERV class in exemplary members of the Auckland Island herd. As described herein, it would be advantageous to have donor pigs that lack PERV-C.

Methods

PERV class was determined using the methods described herein to determine PERV copy number (see Example 2 herein). PERV copy number is determined using specific primers for the pol region of the provirus. This method is able to detect proviral copies of the different PERV classes A, B, and C.

Results

Two pigs in the AI herd (pigs #102 and #212) were found to be negative for PERV-C. Advantageously, pig #102 is also blood group 0, and thereby is an excellent candidate for donor breeding.

CONCLUSION

The breeding methods of the invention are capable of producing swine particularly suited to use as donors for xenotransplantation. Organs, tissues or cells can be isolated from such swine, and preferably are thereby free of infectious microorganisms, have low copy number of PERV, lack PERV-C, and are of blood group O. Such cells are expected to be particularly suited to xenotransplantation, at least in part by virtue of presenting the lowest potential risk of transmission of infectious agents and/or of immunological rejection.

PUBLICATIONS

1. Mills J N, et al., 1999. Emerg Infect Dis, 5:135-42.
2. Allan G M., & J A Ellis., 2000. Porcine circoviruses: a review. J. Vet. Diagn. Investig. 12:3-14.
3. Mueller N J, et al., 2002. Activation of cytomegalovirus in pig-to-primate organ transplantation. J. Virol. 76:4734-4740.
4. Hattermann K, et al., 2004. Infection studies on human cell lines with porcine circovirus type 1 and porcine circovirus type 2. Xenotransplantation 11:284-294.
5. Patience C, et al., 1997. Infection of human cells by an endogenous retrovirus of pigs. Nat. Med. 3:282-286.
6. U.S. Pat. No. 6,867,347
7. U.S. Pat. No. 6,469,229
8. LeTissier P. J et al. 1997. Two sets of human-tropic pig retrovirus. Nature, 389:681-682.
9. Takeuchi Y et al. 1998. Host vrange and interferences studies of three classes of pig endogenous retrovirus J Virol, 72:9986-9991.
10. Gemeniano M et al, The infectivity and host range of the ecotopic porcine endogenous retrovirus, PERV-C, is modulated by residues in the C-terminal region of its surface envelope protein. 2006. Virology 346(1):108-17.
11. Edington N, 1999. Cytomegalovirus. In: Straw B E, D'Állaire S, Mengeling W L, Taylor D J, editors. Diseases of swine (8$^{th}$ edition). Ames, Iowa: Iowa State University Press. p 125-131.
12. Ho M, & Drummer J S, 1995. Infections in transplant recipients. In: Mandell L, Bennett J E, Dolin R, editors. Mandell, Douglas and Bennett's principles and practice of infectious diseases. New York: Churchill Livingstone. p. 35-107.
13. Garkaveiko O, et al., 2004. Monitoring for Potentially Xenozoonotic Viruses in New Zealand Pigs. J Med Virol. 72:338-344.
14. Ulrich S, et al., 1999. Characterisation of the DNA polymerase loci of the novel porcine lymphotropic herpesviruses 1 and 2 in domestic and feral pigs. J Gen Virol 80(12):3199-3205.
15. Brewer L A, et al., 2001. Porcine encephalomyocarditis virus persists in pig myocardium and infects human myocardial cells. J Virology 75(23):11621-11629.
16. Horner G, 1991. Pig circovirus antibodies present in New Zealand pigs. Survey Wellington 18:23.
17. Tischer I, et al., 1974. Characterisation of papovavirus- and picornavirus-like particles in permanent pig kidney cell lines. Zentralblatt fur Bacteriologie Microbiologie und Hygiene seres A 226:153-167.
18. Tischer I, et al., 1995. Presence of antibodies reacting with porcine circovirus in sera of humans, mice, and cattle. Arch Virol 140:1427-1439.
19. Rodriguez-Arrioja G M, et al., 1999. Aujeszky's disease virus infection concurrent with postweaning multisystemic wasting syndrome in pigs. Vet Rec 144:152-153.
20. O'Connor B, et al., 2001. Multiple porcine circovirus 2-associated abortions and reproductive failure in a multi-site swine production unit. Can Vet J 42:551-553.
21. Hatterman K, & Mankertz A., 2002. Infection studies on human cell-lines with porcine circovirus type 1 and type 2. The World of Microbes, Paris, 27 Jul.-1 Aug. 2002, V-385: 132.
22. Kiupel M, et al., 2001. Viral replication and lesions in BALB/c mice experimentally inoculated with porcinecirco virus isolated from a pig with postweaning multisystemic wasting disease. Vet Pathol 38:74-82.
23. WO 01/52871
24. WO 02/32437
25. WO 2004/113516
26. WO 03/027270
27. WO 00/66188
28. NZ 532057/532059/535131
29. U.S. Pat. No. 6,610,288
30. Hamel A L, et al., 1999. PCR assay for detecting porcine cytomegalovirus. J Clin Microbiol 37:3767-3768.
31. Ehlers B, et al., 1999. Detection of two novel porcine herpesviruses with high similarity to gammaherpesviruses. J Gen Virol 80:971-978.
32. Vanderhallen H, & Koenen F, 1998. Identification of encephalomyocarditis virus in clinical samples by reverse transcription-PCR followed by genetic typing using sequence analysis. J Clin Microbiol 36:3463-3467.
33. Larochelle R, et al., 1999. Typing of porcine circovirus in clinical specimens by multiplex PCR. J Virol Methods 80:69-75.
34. Erker J C, et al., 1999. Rapid detection of hepatitis E virus RNA by reverse transcription-polymerase chain reaction using universal oligonucleotide primers. J Virol Methods 81:109-113.

All patents, publications, scientific articles, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of various embodiments or preferred embodiments and are exemplary only and not intended as limitations on the scope of the invention. Other objects, aspects, examples and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A method of breeding a herd of pigs that are free of infectious microorganisms and have a PERV copy number per cell from 1 to 30 and
   (i) are of blood group O; or
   (ii) are lacking PERV-C; or
   (iii) are of blood group O and are lacking PERV-C,
   said method comprising the steps:
   (a) selecting male and female Auckland Island swine having a favorable microorganism profile,
   (b) mating male and female swine selected in step (a),
   (c) selecting progeny produced by step (b) that have a favorable microorganism profile and a PERV copy number per cell from 1 to 30 and
       (i) are of blood group O; or
       (ii) are lacking PERV-C; or
       (iii) are of blood group O and are lacking PERV-C,
   wherein the favorable microorganism profile comprises no detectable levels of herpesvirus, porcine lymphotrophic herpesvirus (PLHV), pig cytomegalovirus (PCMV), encephalomyocarditis virus (EMCV), pig circovirus (PCV), hepatitis E virus (HEV), Toxoplasma, eperythrozoon, brucella, listeria, mycobacterium TB, leptospirillum, haemophilus suis, any virus causing porcine respiratory reproductive syndrome, any virus causing rabies, any virus causing pseudorabies, parvovirus, any virus causing swine vesicular disease, porcine polio virus (techen), any virus causing hemagglutinating encephalomyocarditis, swine influenza type A, adenovirus, transmissible gastroenteritis virus and vesicular stomatitis virus, a hard return thereby providing a herd of pigs that are free of infectious microorganisms and have a PERV copy number per cell from 1 to 30 and
   (i) are of blood group O; or
   (ii) are lacking PERV-C; or
   (iii) are of blood group O and are lacking PERV-C,
   whereby the progeny selected in step (c) are suitable for use as a donor source of cells or tissue for xenotransplantation.

2. A method of breeding a herd of pigs that are free of infectious microorganisms and have a PERV copy number per cell from 1 to 30, said method comprising the steps:
   (a) selecting male and female Auckland Island swine having a favorable microorganism profile,
   (b) mating male and female swine selected in step (a),
   (c) selecting progeny produced by step (b) that have a favorable microorganism profile and a PERV copy number per cell from 1 to 30;
   wherein the favorable microorganism profile comprises no detectable levels of herpesvirus, porcine lymphotrophic herpesvirus (PLHV), pig cytomegalovirus (PCMV), encephalomyocarditis virus (EMCV), pig circovirus (PCV), hepatitis E virus (HEV), Toxoplasma, eperythrozoon, brucella, listeria, mycobacterium TB, leptospirillum, haemophilus suis, any virus causing porcine respiratory reproductive syndrome, any virus causing rabies, any virus causing pseudorabies, parvovirus, any virus causing swine vesicular disease, porcine polio virus (techen), any virus causing hemagglutinating encephalomyocarditis, swine influenza type A, adenovirus, transmissible gastroenteritis virus and vesicular stomatitis virus, thereby providing a herd of pigs that are free of infectious microorganisms and have a PERV copy number per cell from 1 to 30, and
   whereby the progeny selected in step (c) are suitable for use as a donor source of cells or tissue for in xenotransplantation.

3. The method according to claim 2 wherein the male and/or female swine of step (b) and/or the progeny of step (c) have a PERV copy number per cell from 1 to 25.

4. The method according to claim 2 wherein the male and/or female swine of step (b) and/or the progeny of step (c) have a PERV copy number per cell from 1 to 20.

5. The method according to claim 2 wherein the male and/or female swine of step (b) and/or the progeny of step (c) have a PERV copy number per cell from 1 to 14.

6. The method according to claim 2 wherein the male and/or female swine of step (b) and/or the progeny of step (c) have a PERV copy number per cell from 1 to 10.

7. The method according to claim 2 wherein the male and/or female swine of step (b) and/or the progeny of step (c) have a PERV copy number per cell from 1 to 5.

8. The method according to claim 2 wherein male and female progeny selected in step (c) are mated to produce further progeny.

9. The method according to claim 2 wherein said method includes an additional step of screening for a blood group to match either a potential xenotransplant recipient or to match the antigen profile of serum used in in vitro culture, wherein the matched blood group reduces tissue rejection and/or cell damage mediated by immune reactions.

10. The method according to claim 9 wherein the swine selected in step (a) are of blood group O or are lacking PERV-C.

11. The method according to claim 9 wherein the progeny selected in step (c) are of blood group O or are lacking PERV-C.

12. The method according to claim 2 wherein said method includes an additional step of screening for one or more immunogenic antigens present on cell surfaces.

* * * * *